US008871716B2

(12) United States Patent
Kim et al.

(10) Patent No.: US 8,871,716 B2
(45) Date of Patent: Oct. 28, 2014

(54) USE OF ANTIMICROBIAL PEPTIDES IN REGENERATION OF SKIN CELLS

(75) Inventors: Sun-Chang Kim, Daejeon (KR); Da-Jung Kim, Daejeon (KR); Su-A Jang, Daejeon (KR); Bong Hyun Sung, Daejeon (KR); Ki-Jung Lim, Daejeon (KR); Ju-Ri Shin, Daejeon (KR); Young Woong Lee, Daejeon (KR)

(73) Assignees: Korea Advanced Institute of Science and Technology, Daejeon (KR); Intelligent Synthetic Biology Center, Daejeon (KR)

( * ) Notice: Subject to any disclaimer, the term of this patent is extended or adjusted under 35 U.S.C. 154(b) by 0 days.

(21) Appl. No.: 13/095,763

(22) Filed: Apr. 27, 2011

(65) Prior Publication Data

US 2012/0088733 A1 Apr. 12, 2012

Related U.S. Application Data

(63) Continuation of application No. PCT/KR2010/009558, filed on Dec. 30, 2010.

(30) Foreign Application Priority Data

Oct. 8, 2010 (KR) ........................ 10-2010-0098259

(51) Int. Cl.
*A61K 8/64* (2006.01)
*A61K 38/00* (2006.01)
*A61K 38/10* (2006.01)

(52) U.S. Cl.
CPC ...................................... *A61K 38/10* (2013.01)
USPC ................... 514/18.6; 514/2.3; 514/2; 514/6; 514/9.4

(58) Field of Classification Search
None
See application file for complete search history.

(56) References Cited

U.S. PATENT DOCUMENTS

2002/0110555 A1* 8/2002 Lee ............................ 424/130.1

FOREIGN PATENT DOCUMENTS

| KR | 10-2001-0081188 A | 8/2001 |
| KR | 10-2004-0012396 A | 2/2004 |
| KR | 10-2004-0029072 A | 4/2004 |
| KR | 836596 B1 * | 6/2008 |
| KR | 100836596 | 6/2008 |
| KR | 10-2010-0060123 A | 6/2010 |
| KR | 10-2010-0060949 A | 6/2010 |
| KR | 10-2011-0013466 A | 2/2011 |
| WO | 2011/149173 A1 | 12/2011 |

OTHER PUBLICATIONS

Kim et al. KR 836596, English Translation.*
Park et al. (J Biological Chemistry, 279:14, pp. 13896-13901, 2004).*
English machine translation of KR1008365596 63 pages, Jun. 2008, translation obtained in 2014.*
Tokumaru, et al., Induction of Keratinocyte Migration Via Transactivation of the Epidermal Growth Factor Receptor by the Antimicrobial Peptide LL-37, J. Immunol., 2005, 175: p. 4662-4668.
Mantyla, et al., "Effect of temporin A modifications on its cytotoxicity and antimicrobial activity", APMIS, 2005, vol. 113, pp. 497-505.
Extended European Search Report, European Patent Application No. 10824258.7, Date of Issuance: Apr. 11, 2014.
Chu, Yaping et al., "Nurr1 in Parkinson's Disease and Related Disorders", The Journal of Comparative Neurology, 2006, 494:495-514.
Suk Kyoungho, "Research focus on natural products and the body's immune and inflammatory systems," New York: Nova Biomedical Books, 2007, pp. 44-47.
Xu, Wen-Cheng et al., "Phytochemical and Biological Studies of the Plants from the Genus *Daphne*", Chemistry & Biodiversity, 2011, vol. 8, pp. 1215-1233.
Zhang, Shixuan et al., "Evaluation of Daphne genkwa Diterpenes: Fingerprint and Quantitative Analysis by High Performance Liquid Chromatography", Phytochemical Analysis, 2007, 18: 91-97.

* cited by examiner

*Primary Examiner* — James H Alstrum Acevedo
*Assistant Examiner* — Li Lee
(74) *Attorney, Agent, or Firm* — Gavrilovich, Dodd & Lindsey LLP; Joseph R. Baker, Jr.

(57) ABSTRACT

Disclosed are novel antimicrobial peptides which can promote the regeneration of skin cells, thus healing wounds. Pharmaceutical compositions comprising the peptides as active ingredients are also provided for wound healing and skin rejuvenation. The antimicrobial peptides exhibit inhibitory activity against antibiotic-resistant strains, and their antimicrobial activity is maintained without loss of structural stability even under a high salt condition. Also, being proven to promote the migration and regeneration of skin cells in mice as well as in vitro, the antimicrobial peptides may be widely used as an agent for regenerating skin cells. Further, they can find applications in various fields including the medical industry and the cosmetic industry. Hence, the novel antimicrobial peptides are anticipated to have considerable repercussions in the market for antibiotics, wound healing agents and cosmetics.

5 Claims, 3 Drawing Sheets

USE OF ANTIMICROBIAL PEPTIDES IN REGENERATION OF SKIN CELLS

CROSS-REFERENCE TO RELATED PATENT APPLICATIONS

This application is a continuation application under 35 U.S.C. §365(c) of International Application No. PCT/KR2010/009558, filed Dec. 30, 2010 designating the United States. This application further claims the benefit of the earlier filing date under 35 U.S.C. §365(b) of Korean Patent Application No. 10-2010-0098259 filed Oct. 8, 2010. This application incorporates herein by reference the International Application No. PCT/KR2010/009558 and the Korean Patent Application No. 10-2010-0098259 in their entirety.

TECHNICAL FIELD

The present invention relates to a pharmaceutical composition for wound healing, comprising an antimicrobial peptide as an active ingredient. More particularly, the present invention relates to a composition for wound healing or rejuvenating the skin, comprising as an active ingredient an antimicrobial peptide useful for promoting the regeneration of skin cells to heal wounds, a method for healing wounds or regenerating skin cells by applying the composition to wounds or damaged skin, and the use of a peptide.

BACKGROUND

Wound healing agents, including antibiotics for preventing microbe-induced secondary infection, have evolved over the course of a long history, and now a variety of wound healing agents are being developed and used. Since the discovery of penicillin by Fleming in the twentieth century, the development of antibiotics has made great advances. In the beginning, wound healing agents comprised antibiotics alone, but recently these have been used in combination with a protein agent for promoting the regeneration of injured cells, such as EGF (epidermal growth factor), a cytokine, interleukins, or TGF-β (transforming growth factor-beta) to elevate wound healing potentials. However, the emergence of bacteria resistant to pre-existing antibiotics has necessitated the continued development of novel antibiotics.

So long as chemicals with antibiotic activity are employed against bacterial infections, resistance of bacteria to antibiotics is now regarded as inevitable. Hence, what is important for the development of novel antibiotics is not to make bacteria no longer resistant to antibiotics, but to reduce the occurrence and spread of antibiotic resistance.

In an attempt to search for efficient solutions to infections with antibiotic-resistant bacteria, many researchers have paid intensive attention to a new concept of antibiotics. On the other hand, most protein additives are not widely used in wound healing agents because they are very expensive and unstable. Steroids that are found in most of the currently available wound healing agents have the side effect of causing dermatitis. Given this background, antimicrobial peptides are arising as promising alternatives because they show excellent wound healing activity and have almost no side effects on the skin. Many attempts have been made to employ naturally occurring antimicrobial peptides themselves or synthetic analogs thereof. Their practical applications are, however, imparted with lots of limitations because their antimicrobial activity is accompanied by erythrocytolysis. Therefore, extensive studies are being concentrated on the development of peptides that show high antimicrobial activity without cytotoxicity.

Antimicrobial peptides are widely distributed in nature and generally are as short as 5-50 amino acid residues in length. They are almost free of influence by acid, alkali and heat, and can be readily degraded after performing their antimicrobial activity. Among them, cathelicidin LL-37 and magainin2, a magainin derivative, function as potent antibiotics as well as having the ability to regenerate cells. Their ability to regenerate cells starts with the association of the peptides with EGFR (epidermal growth factor receptor) to which EGF (epidermal growth factor), responsible for cell regeneration, binds. It is also found that antimicrobial peptides having alpha-helix structures, like LL-37, can regenerate cells (TokuMaru S. et al., *J Immunol*. Japan, 175(7), p 4662-4668, 2005).

The use of the antimicrobial peptides in wound healing is being studied by various research groups. For example, human cathelicidin LL-37, ceragenin, cecropin, bacteriocin, fungal defensin and plectasin are in pre-clinical trials for use as wound healing agents, while pexiganan (MSI-78), a derivative of frog magainin, and iseganan (IB-367), a derivative of pig protegrin, are in phase 3 clinical trials for treatment of diabetic foot ulcer and oral mucositis. However, their in-vivo instability, which results in a decrease in wound healing potential, must be negated before they can be used as wound healing agents.

Leading to the present invention, intensive and thorough research into antimicrobial peptides having structural stability and high antimicrobial activity under the physiological conditions, conducted by the present inventors, resulted in the finding that some of the antimicrobial peptides, which were previously developed by the present inventors (Korean Patent No. 10-0836596) to retain high antimicrobial activity even at as high a salt concentration as under physiological conditions, exhibited the activity of promoting the migration and regeneration of skin cells and thus reducing the period of time required for wound healing in vitro and in vivo.

SUMMARY

It is an aspect of the present invention to provide a pharmaceutical composition for wound healing, comprising as an active ingredient a peptide having a sequence represented by the general formula I (SEQ ID NO. 3):

[General Formula I]
[N-terminal end-APKAMY$^1$Y$^2$Y$^3$Y$^4$Y$^5$Y$^6$Y$^7$Y$^8$LQKKGI-C-terminal end]

wherein,

Y$^1$ represents one basic amino acid residue;

each of Y$^2$ and Y$^3$ represents one hydrophobic amino acid residue, which may be the same or different;

each of Y$^4$ and Y$^5$ represents one basic amino acid residue, which may be the same or different;

each of Y$^6$ and Y7$^3$ represents one hydrophobic amino acid residue, which may be the same or different; and Y$^8$ represents one basic amino acid residue.

It is another aspect of the present invention to provide a composition for regenerating skin cells, comprising the peptide as an active ingredient.

It is another aspect of the present invention to provide a cosmetic for skin rejuvenation, comprising the peptide as an active ingredient.

It is a further aspect of the present invention to provide a method for healing a wound of an animal and regenerating skin cells, comprising treating a subject in need thereof with a composition comprising the peptide as an active ingredient.

It is still a further aspect of the present invention to provide the use of the peptide in the preparation of a composition for wound healing and skin cell regeneration.

In one aspect, a pharmaceutical composition for wound healing is provided. The pharmaceutical composition may comprise a peptide having a sequence represented by the general formula I (SEQ ID NO.3):

[General Formula I]
[N-terminal end-APKAMY$^1$Y$^2$Y$^3$Y$^4$Y$^5$Y$^6$Y$^7$Y$^8$LQKKGI-C-terminal end]

wherein, $Y^1$ represents one basic amino acid residue; each of $Y^2$ and $Y^3$ represents one hydrophobic amino acid residue, which may be the same or different; each of $Y^4$ and $Y^5$ represents one basic amino acid residue, which may be the same or different; each of $Y^6$ and $Y^7$ represents one hydrophobic amino acid residue, which may be the same or different; and $Y^8$ represents one basic amino acid residue. In one embodiment, the basic amino acid residue may be lysine, arginine or histidine. In another embodiment, the hydrophobic amino acid residue may be alanine, valine or leucine. In still another embodiment, the peptide of general formula I may be amidated at the C-terminal end thereof. In still another embodiment, the composition may perform wound healing by regenerating skin cells. In still another embodiment, the composition may further exhibit antimicrobial activity at a salt concentration of from 100 to 200 mM. In still another embodiment, the composition may further comprise a pharmaceutically acceptable carrier, excipient or diluent. In still another embodiment, the peptide of the general formula I may have an amino acid sequence of SEQ ID NO. 1 or 2. In still another embodiment, the peptide in the composition may be present at a concentration of from 0.5 to 2 µM.

In another aspect, a composition for regenerating skin cells is provided. The composition for regenerating skin cell may comprise a peptide having a sequence represented by the general formula I (SEQ ID NO. 3):

[General Formula I]
[N-terminal end-APKAMY$^1$Y$^2$Y$^3$Y$^4$Y$^5$Y$^6$Y$^7$Y$^8$LQKKGI-C-terminal end]

wherein, $Y^1$ represents one basic amino acid residue; each of $Y^2$ and $Y^3$ represents one hydrophobic amino acid residue, which may be the same or different; each of $Y^4$ and $Y^5$ represents one basic amino acid residue, which may be the same or different; each of $Y^6$ and $Y^7$ represents one hydrophobic amino acid residue, which may be the same or different; and $Y^8$ represents one basic amino acid residue. In one embodiment, the basic amino acid residue may be lysine, arginine or histidine. In another embodiment, the hydrophobic amino acid residue may be alanine, valine or leucine. In still another embodiment, the peptide of general formula I may be amidated at the C-terminal end thereof. In still another embodiment, the composition may further exhibit antimicrobial activity at a salt concentration of from 100 to 200 mM. In still another embodiment, the composition may further comprise a pharmaceutically acceptable carrier, excipient or diluent. In still another embodiment, the peptide of the general formula I may have an amino acid sequence of SEQ ID NO. 1 or 2. In still another embodiment, the peptide in the composition may be present at a concentration of from 0.5 to 2 µM.

In still another aspect, a cosmetic for skin rejuvenation, comprising the foregoing composition for regenerating skin cells is provided.

In still another aspect, a method for healing a wound of an animal is provided. The method may comprise treating the wound with a peptide having a sequence represented by the general formula I (SEQ ID NO.3):

[General Formula I]
[N-terminal end-APKAMY$^1$Y$^2$Y$^3$Y$^4$Y$^5$Y$^6$Y$^7$Y$^8$LQKKGI-C-terminal end]

wherein, $Y^1$ represents one basic amino acid residue; each of $Y^2$ and $Y^3$ represents one hydrophobic amino acid residue, which may be the same or different; each of $Y^4$ and $Y^5$ represents one basic amino acid residue, which may be the same or different; each of $Y^6$ and $Y^7$ represents one hydrophobic amino acid residue, which may be the same or different; and $Y^8$ represents one basic amino acid residue. In one embodiment, the basic amino acid residue may be lysine, arginine or histidine. In another embodiment, the hydrophobic amino acid residue may be alanine, valine or leucine. In still another embodiment, the peptide of general formula I may be amidated at the C-terminal end thereof. In still another embodiment, the method may further exhibit antimicrobial activity at a salt concentration of from 100 to 200 mM. In still another embodiment, the method may further comprise a pharmaceutically acceptable carrier, excipient or diluent. In still another embodiment, the peptide of general formula I may have an amino acid sequence of SEQ ID NO. 1 or 2. In still another embodiment, the peptide may be present at a concentration of from 0.5 to 2 µM.

In still another aspect, a method for regenerating skin cells is provided. The method may comprise treating an injured skin with a peptide having a sequence represented by the general formula I (SEQ ID NO.3):

[General Formula I]
[N-terminal end-APKAMY$^1$Y$^2$Y$^3$Y$^4$Y$^5$Y$^6$Y$^7$Y$^8$LQKKGI-C-terminal end]

wherein, $Y^1$ represents one basic amino acid residue; each of $Y^2$ and $Y^3$ represents one hydrophobic amino acid residue, which may be the same or different; each of $Y^4$ and $Y^5$ represents one basic amino acid residue, which may be the same or different; each of $Y^6$ and $Y^7$ represents one hydrophobic amino acid residue, which may be the same or different; and $Y^8$ represents one basic amino acid residue. In one embodiment, the basic amino acid residue may be lysine, arginine or histidine. In another embodiment, the hydrophobic amino acid residue may be alanine, valine or leucine. In still another embodiment, the peptide of general formula I may be amidated at the C-terminal end thereof. In still another embodiment, the method may further exhibit antimicrobial activity at a salt concentration of from 100 to 200 mM. In still another embodiment, the method may further comprise a pharmaceutically acceptable carrier, excipient or diluent. In still another embodiment, the peptide may have an amino acid sequence of SEQ ID NO. 1 or 2. In still another embodiment, the method may be present at a concentration of from 0.5 to 2 µM.

In still another aspect, a method of using a peptide having a sequence represented by the general formula I in preparing a pharmaceutical composition for wound healing is provided. The peptide may be defined as follows:

[General Formula I]
(SEQ ID NO. 3)
[N-terminal end-APKAMY$^1$Y$^2$Y$^3$Y$^4$Y$^5$Y$^6$Y$^7$Y$^8$LQKKGI-C-terminal end]

wherein, $Y^1$ represents one basic amino acid residue; each of $Y^2$ and $Y^3$ represents one hydrophobic amino acid residue, which may be the same or different; each of $Y^4$ and $Y^5$ represents one basic amino acid residue, which may be the same or different; each of $Y^6$ and $Y^7$ represents one hydrophobic amino acid residue, which may be the same or different; and $Y^8$ represents one basic amino acid residue. In one embodiment, the basic amino acid residue may be lysine, arginine or histidine. In another embodiment, the hydrophobic amino acid residue may be alanine, valine or leucine. In still another embodiment, the peptide of general formula I may be amidated at the C-terminal end thereof. In still another embodiment, the method may be designed to heal a wound by regenerating skin cells. In still another embodiment, the method may further exhibit antimicrobial activity at a salt concentration of from 100 to 200 mM. In still another embodiment, the method may further comprise a pharmaceutically acceptable carrier, excipient or diluent. In still another embodiment, the peptide may have an amino acid sequence of SEQ ID NO. 1 or 2. In still another embodiment, the peptide may be present at a concentration of from 0.5 to 2 µM.

In still another aspect, a method of using a peptide having a sequence represented by the general formula I in preparing a composition for regenerating skin cells is provided. The peptide may be defined as follows:

[General Formula I]
(SEQ ID NO. 3)
[N-terminal end-APKAMY$^1$Y$^2$Y$^3$Y$^4$Y$^5$Y$^6$Y$^7$Y$^8$LQKKGI-C-terminal end] of SEQ ID NO. 3 wherein, $Y^1$ represents one basic amino acid residue; each of $Y^2$ and $Y^3$ represents one hydrophobic amino acid residue, which may be the same or different; each of $Y^4$ and $Y^5$ represents one basic amino acid residue, which may be the same or different; each of $Y^6$ and $Y^7$ represents one hydrophobic amino acid residue, which may be the same or different; and $Y^8$ represents one basic amino acid residue. In one embodiment, the basic amino acid residue may be lysine, arginine or histidine. In another embodiment, the hydrophobic amino acid residue may be alanine, valine or leucine. In still another embodiment, the peptide of general formula I may be amidated at the C-terminal end thereof. In still another embodiment, the method may further exhibit antimicrobial activity at a salt concentration of from 100 to 200 mM. In still another embodiment, the method may further comprise a pharmaceutically acceptable carrier, excipient or diluent. In still another embodiment, the peptide may have an amino acid sequence of SEQ ID NO. 1 or 2. In still another embodiment, the peptide may be present at a concentration of from 0.5 to 2 µM.

In still another aspect, a cosmetic for skin rejuvenation is provided. The cosmetic may comprise a peptide having a sequence represented by the general formula I (SEQ ID NO.3):

[General Formula I]
[N-terminal end-APKAMY$^1$Y$^2$Y$^3$Y$^4$Y$^5$Y$^6$Y$^7$Y$^8$LQKKGI-C-terminal end]

wherein, $Y^1$ represents one basic amino acid residue; each of $Y^2$ and $Y^3$ represents one hydrophobic amino acid residue, which may be the same or different; each of $Y^4$ and $Y^5$ represents one basic amino acid residue, which may be the same or different; each of $Y^6$ and $Y^7$ represents one hydrophobic amino acid residue, which may be the same or different; and $Y^8$ represents one basic amino acid residue.

In still another aspect, a method for healing a wound of an animal is provided. The method may comprise treating the wound with a peptide having a sequence represented by the general formula I (SEQ ID NO.3):

[General Formula I]
[N-terminal end-APKAMY$^1$Y$^2$Y$^3$Y$^4$Y$^5$Y$^6$Y$^7$Y$^8$LQKKGI-C-terminal end]

wherein, $Y^1$ represents one basic amino acid residue; each of $Y^2$ and $Y^3$ represents one hydrophobic amino acid residue, which may be the same or different; each of $Y^4$ and $Y^5$ represents one basic amino acid residue, which may be the same or different; each of $Y^6$ and $Y^7$ represents one hydrophobic amino acid residue, which may be the same or different; and $Y^8$ represents one basic amino acid residue. In one embodiment, the basic amino acid residue may be lysine, arginine or histidine. In another embodiment, the hydrophobic amino acid residue may be alanine, valine or leucine. In still another embodiment, the peptide of general formula I may be amidated at the C-terminal end thereof. In still another embodiment, the method further exhibit antimicrobial activity at a salt concentration of from 100 to 200 mM. In still another embodiment, the method may further comprise a pharmaceutically acceptable carrier, excipient or diluent. In still another embodiment, the peptide may have an amino acid sequence of SEQ ID NO. 1 or 2. In still another embodiment, the peptide may be present at a concentration of from 0.5 to 2 µM.

In still another aspect, a method for regenerating skin cells is provided. The method may comprise treating an injured skin with a peptide having a sequence represented by the general formula I (SEQ ID NO.3):

[General Formula I]
[N-terminal end-APKAMY$^1$Y$^2$Y$^3$Y$^4$Y$^5$Y$^6$Y$^7$Y$^8$LQKKGI-C-terminal end]

wherein, $Y^1$ represents one basic amino acid residue; each of $Y^2$ and $Y^3$ represents one hydrophobic amino acid residue, which may be the same or different; each of $Y^4$ and $Y^5$ represents one basic amino acid residue, which may be the same or different; each of $Y^6$ and $Y^7$ represents one hydrophobic amino acid residue, which may be the same or different; and $Y^8$ represents one basic amino acid residue. In one embodiment, the basic amino acid residue may be lysine, arginine or histidine. In another embodiment, the hydrophobic amino acid residue may be alanine, valine or leucine. In still another embodiment, the peptide of general formula I may be amidated at the C-terminal end thereof. In still another embodiment, the method may further exhibit antimicrobial activity at a salt concentration of from 100 to 200 mM. In still another embodiment, the method may further comprise a pharmaceutically acceptable carrier, excipient or diluent. In still another embodiment, the peptide may have an amino acid sequence of SEQ ID NO. 1 or 2. In still another embodiment, the peptide may be present at a concentration of from 0.5 to 2 μM.

DETAILED DESCRIPTION OF THE EMBODIMENTS

Figure 1:
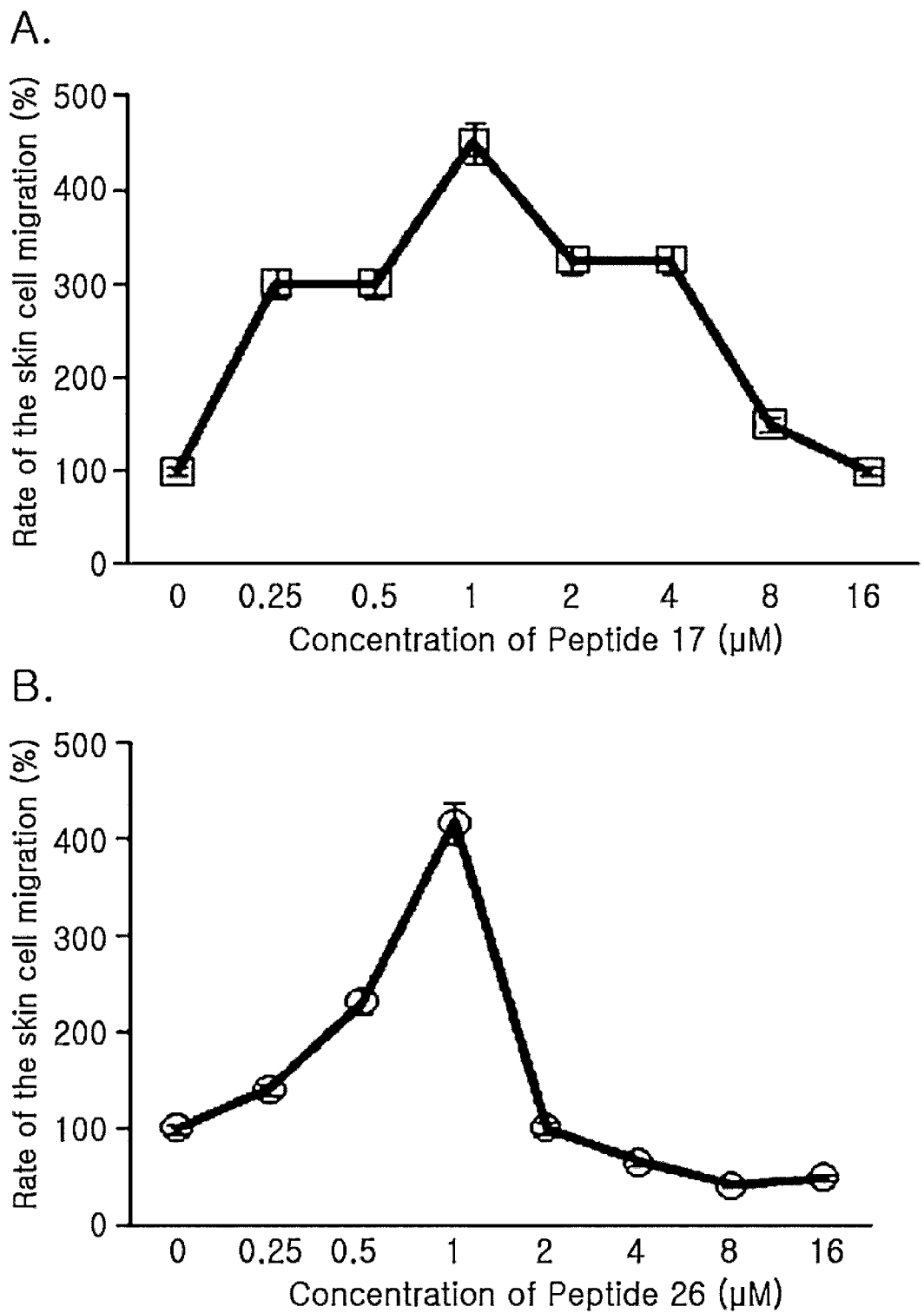
FIG. 1 is of graphs showing migration rates of skin cells caused by the antimicrobial peptides.

In accordance with an aspect thereof, the present invention pertains to a pharmaceutical composition for wound healing, comprising as an active ingredient a peptide having a sequence represented by the following general formula I (SEQ ID NO.3):

[General Formula I]
[N-terminal end-APKAMY$^1$Y$^2$Y$^3$Y$^4$Y$^5$Y$^6$Y$^7$Y$^8$LQKKGI-C-
    terminal end]

wherein,

Y$^1$ represents one basic amino acid residue;

each of Y$^2$ and Y$^3$ represents one hydrophobic amino acid residue, which may be the same or different;

each of Y$^2$ and Y$^3$ represents one basic amino acid residue, which may be the same or different;

each of Y$^2$ and Y$^3$ represents one hydrophobic amino acid residue, which may be the same or different; and Y$^8$ represents one basic amino acid residue.

No limitations are imparted to the basic amino acids available for the present invention, but lysine, arginine and histidine are preferable in some embodiments. Preferred examples of the hydrophobic amino acids useful in some embodiments of the present invention include, but are not limited to, alanine, valine, and leucine. The general formula I is preferably amidated at the C terminus. The composition may further comprise pharmaceutically available carriers, excipients and/or diluents. In the composition, the peptide is preferably contained at a concentration of from 0.5 to 2 μM, to which, however, the present invention is not limited.

The amino acid sequence of the present invention is expressed with abbreviations for amino acid residues according to the IUPAC-IUB nomenclature, as follows (Table 1).

TABLE 1

| IUPAC-IUB nomenclature | | | |
|---|---|---|---|
| Alanine | A | Arginine | R |
| Asparagine | N | Aspartic acid | D |
| Cysteine | C | Glutamic acid | E |
| Glutamine | Q | Glycine | G |
| Histidine | H | Isoleucine | I |
| Leucine | L | Lysine | K |
| Methionine | M | Phenylalanine | F |
| Proline | P | Serine | S |

TABLE 1-continued

| IUPAC-IUB nomenclature | | | |
|---|---|---|---|
| Threonine | T | Tryptophan | W |
| Tyrosine | Y | Valine | V |

Turning to the structure of the antimicrobial peptide according to some embodiments of the present invention, it comprises a core motif in which basic amino acid residues and hydrophobic amino acid residues are located in an alternating pattern, with the two capping motifs APKAM (N) and LQKKGI (C) introduced respectively into the N- and C-terminal ends thereof, which forms a secondary structure of alpha-helix. The alpha-helical structure provides the peptides according to some embodiments of the present invention with stabilization irrespective of salt concentration, thus giving rise to an increase in the antimicrobial activity of the peptides. Certain embodiments of the present invention may employ any amino acid residue as long as it is hydrophobic. Preferable examples of the hydrophobic amino acid residues include alanine, valine and leucine, but are not limited thereto.

As used herein, the term "basic amino acid residue" refers to an amino acid residue the side chain of which shows basicity and is positively charged in a neutral pH range. Among them are histidine, arginine and lysine.

In the sequence formula, the basic amino acid residue may be preferably arginine or lysine. More preferably, the peptide according to some embodiments of the present invention has an amino acid sequence of SEQ ID NO. 1 or 2. In an embodiment of the present invention, when it has the basic amino acid arginine or lysine at positions X$^1$, X$^3$ and X$^5$ and the hydrophobic amino acid leucine at positions X$^2$ and X$^4$, the peptide of the sequence formula I remains stable even at in-vivo salt concentrations and shows excellent antimicrobial activity (FIGS. 1 and 2) because it maintains an alpha-helix structure. In consideration of the fact that alpha-helical peptides activate EGFR (epidermal growth factor receptor) on the epidermal cells to promote cell regeneration (Tokuaru S. et al., J. Immunol. Japan, 175 (7), p 4662-4668, 2005), it is quite natural that peptides of the sequence formula I other than those of SEQ ID NOS. 1 and 2 also can promote cell regeneration by activating EGFR.

Therefore, the antimicrobial peptides are first found to be effective for healing wounds in some embodiments of the present invention, although they had previously been identified as being antimicrobial.

In an embodiment of the present invention, the peptide of sequence formula I may have an amidated C-terminal end. When amidated at its C-terminal end, the antimicrobial peptide shows more potent inhibitory activity against Gram-positive and Gram-negative bacteria and fungi.

As implied by the term antimicrobial peptide, the composition exhibits excellent antimicrobial activity even at high salt concentrations. The high antimicrobial activity of the peptides according to some embodiments of the present invention even at a high salt concentration was proven in Korean Patent No. 10-0836596. For example, the peptides according to some embodiments of the present invention exhibited inhibitory activity against Gram-positive and Gram-negative bacteria and fungi at a salt concentration of as high as 100 or 200 mM. This antimicrobial activity is based on the stability of the peptides according to some other embodiments of the present invention even at high salt concentrations, suggesting that they can stably maintain their structures at an in vivo salt concentration, thus exerting wound healing potentials in vivo.

The term "antimicrobial peptide", as used herein, refers to a small-molecular weight protein which is typically as short as 5-50 amino acid residues in length and plays an important role as an immunomodulator in innate host defense. Antimicrobial peptides are found among all classes of life and are responsible for defense against local infections by penetrating into and disturbing the membranes of microbes such as bacteria, fungi and viruses. More particularly, the amphipathicity of the antimicrobial peptides allows them to pass through the membrane lipid bilayer of microbes because the cationic charges of the antimicrobial peptides are associated with the anionic charges of the phospholipids of the membrane. Antimicrobial peptides are barely influenced by acid, alkali and heat, but can be readily degraded after they have performed their antimicrobial action.

Preferably, the pharmaceutical composition for wound healing can also regenerate skin cells.

As used herein, the term "wound healing" is intended to refer to a process in which skin cells are restored and protected after an injury.

As used herein, the term "regeneration of skin cells" is intended to mean the promotion of a process in which when skin tissues are partially lost or die due to a disease or injury, skin cells around the injured tissue proliferate and migrate into the lesion site to restore the dead or lost tissues.

When the peptides according to some embodiments of the present invention were applied to wounds, it took a short time to heal the wounds.

Figure 2:
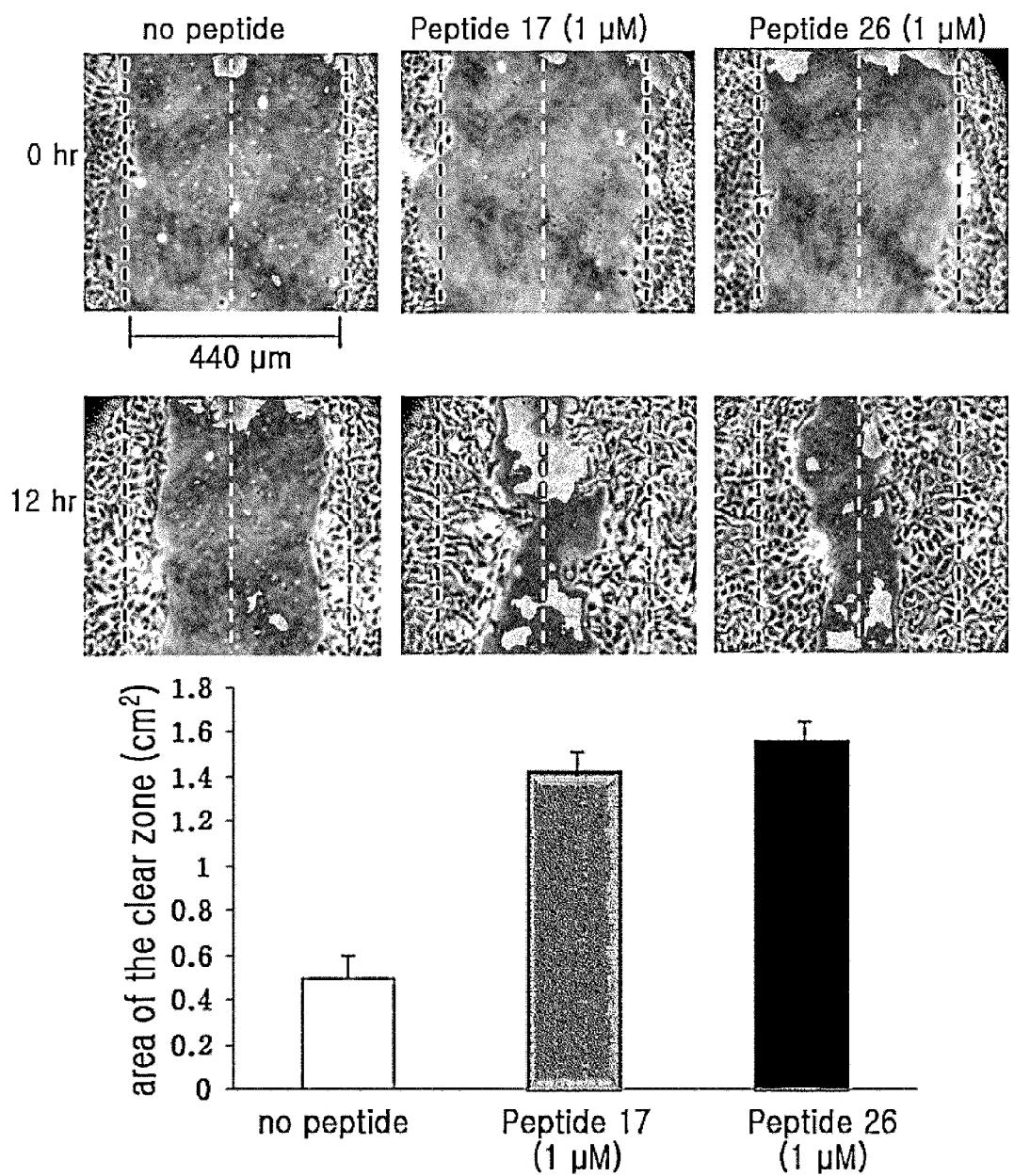
FIG. 2 shows the effects of the antimicrobial peptides on skin cell regeneration in the form of photographs and a graph.
Figure 3:
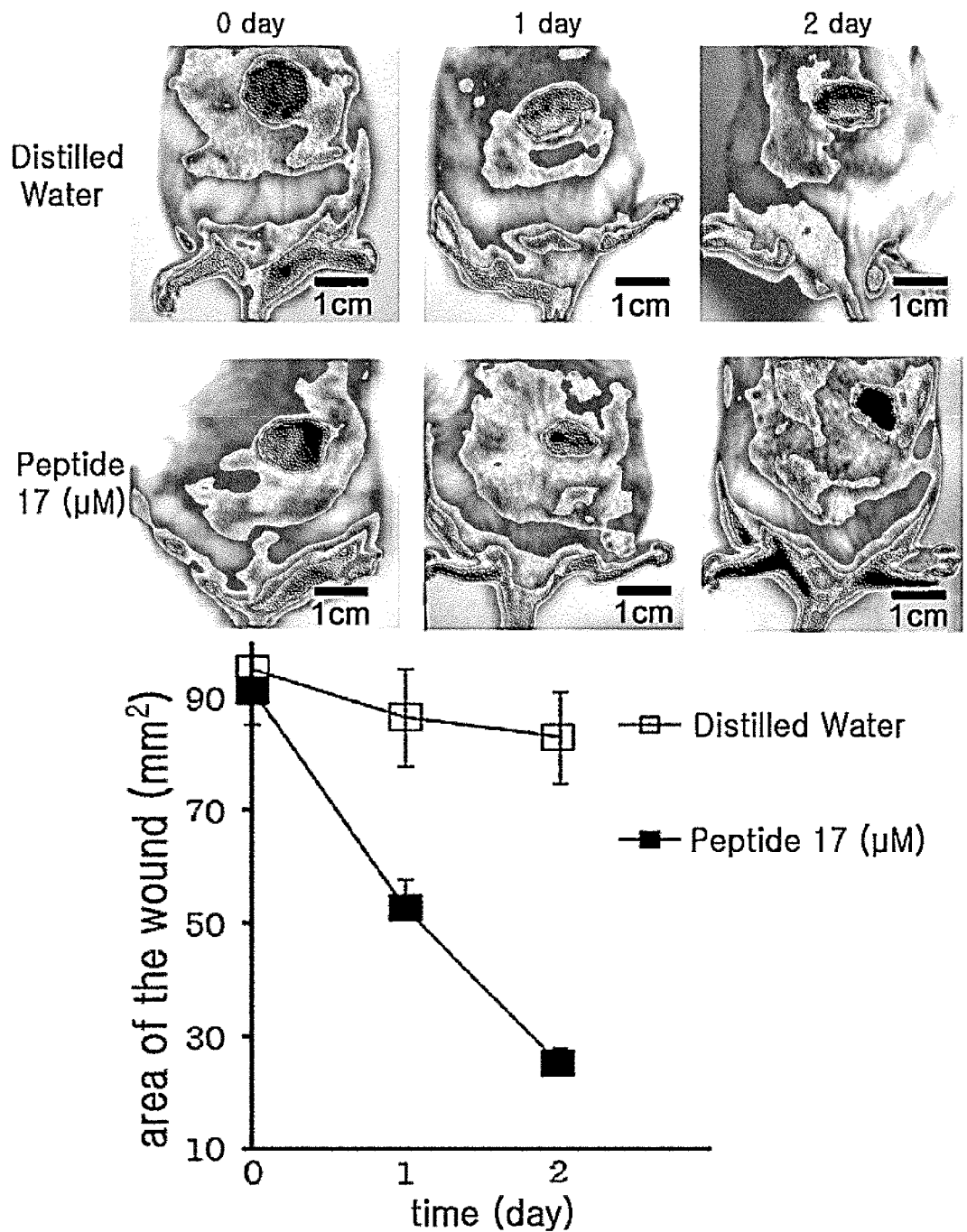
FIG. 3 shows the wound healing effects of the antimicrobial peptides in mouse models. Even at a high salt concentration, the structurally stable antimicrobial peptide 17 was observed to heal wounds formed on the back of the mice. The wound was reduced in area 7-fold faster in mice treated once a day for two days with antimicrobial peptide 17 than in mice treated only with distilled water.

The antimicrobial peptide of SEQ ID NO. 1 or 2 was found to allow the most effective migration of skin cells at a concentration of 11 µM, 4.5 times higher than a control, as measured by a boyden chamber assay (FIG. 1). A scratched wound healing assay demonstrated that 1 µM of the peptide of SEQ ID NO. 1 or 2 induced 2.5-fold fast regeneration of skin cells (FIG. 2). Also, when applied to wound-healing mouse models, the peptide of SEQ ID NO. 1 reduced wound sizes at 7-fold faster rates (FIG. 3). Hence, the peptides according to certain embodiments of the present invention are effective for wound healing and cellular regeneration as well as reducing the time required for wound healing.

The pharmaceutical composition according to some embodiments of the present invention may be made in typical dosage forms, such as injections, pills, tablets, capsules, etc.

Via an appropriate route, the pharmaceutical composition according to some embodiments of the present invention may be introduced into a tissue or organ of interest. So long as it is delivered to the targeted tissue, any route can be used for administration of the pharmaceutical composition according to some certain embodiments of the present invention. For example, the administration may be carried out via intraperitoneal, intravenous, intramuscular, subcutaneous, intradermal, oral, local, intranasal, intrapulmonary, and intrarectal routes, but is not limited thereto. For oral administration, however, the pharmaceutical composition is preferably coated or formulated to protect the active ingredient from being degraded in the stomach because the peptides are digested by pepsin. Preferably, the pharmaceutical composition according to some embodiments of the present invention is administered in an injectable form. Also, the pharmaceutical composition may be administered with the aid of a device through which the active ingredient is delivered to targeted cells.

The pharmaceutical composition according to some embodiments of the present invention may further comprise a pharmaceutically acceptable carrier, excipient or diluent.

As used herein, the term "pharmaceutically acceptable carrier" refers to a vehicle or diluent which does not inhibit the biological activity and properties of the active ingredient and does not irritate the subject. For use in liquid formulations, pharmaceutically acceptable carriers suitable for sterilization are selected. Among them are saline, sterilized water, Ringer's solution, buffered saline, albumin injections, dextrose solutions, maltodextrin solutions, glycerol, ethanol and a combination thereof. Optionally, the composition may further comprise other typical additives, such as antioxidants, buffers, bacteriostats, etc. Also, diluents, dispersants, surfactants, binders and lubricants may be further added to formulate the composition into injections, e.g., solutions, suspensions and emulsions, pills, capsules, or tablets.

In the composition, the peptides may be contained preferably at a concentration of from 0.5 to 2 µM and more preferably at a concentration of 1 µM. In an embodiment, the wound healing activity of the peptides according to some embodiments of the present invention was observed over a concentration range from 0.5 to 2 µM, with a peak at 1 µM (FIG. 1).

In accordance with another aspect thereof, the present invention pertains to a composition for regenerating skin cells, comprising as an active ingredient a peptide having the sequence represented by Formula I.

The peptide is as defined above.

Promoting the regeneration of skin cells, the peptides according to some embodiments of the present invention can reduce the period of time required for wound healing. The composition is also as described above.

In accordance with a further aspect thereof, the present invention pertains to a cosmetic for skin rejuvenation, comprising the composition for regenerating skin cells.

No limitations are imparted to the formulations of the cosmetic for skin rejuvenation. Examples of the cosmetic formulations include solution, suspension, paste, gel, cream, lotion, powder, soap, surfactant-containing cleansers, oil, power foundation, emulsion foundation, wax foundation, and spray, but are not limited thereto. In greater detail, the cosmetic may be formulated into low-irritation cosmetic preparations, skin protective, emollient, nourishing skin lotions, nourishing creams, massage creams, essences, eye cream, cleansing cream, cleansing foam, cleansing water, pack, cream, spray or powder.

In each formulation of the cosmetic for skin rejuvenation, the peptide of sequence formula I may be used in combination with a cosmetically acceptable additive suitable according to the form and use of the cosmetic. For example, the cosmetic may further comprise typical supplements or carriers such as thickeners, stabilizers, solubilizers, vitamins, dyes or aromatics.

In accordance with still a further aspect, the present invention pertains to a method for the treatment of wounds and the rejuvenation of the skin, comprising administering to a subject in need thereof a pharmaceutical composition containing a peptide represented by the sequence formula I as an active ingredient.

As used herein, the term "treatment" is intended to refer to any action resulting in an improvement in wounds or skin rejuvenation or in which wounds or skin rejuvenation is advantageously altered after administration of the composition.

The treatment method using the antimicrobial peptide according to some embodiments of the present invention comprises administering the antimicrobial peptide at a pharmaceutically effective dose. It should be readily understood that an appropriate daily dosage is determined according to the instructions of a physician. Also, the composition may be administered in a single dose or it may be spread out over multiple doses per day. For purposes according to some embodiments of the present invention, however, the therapeutically effective dose for a certain patient is dependent on various factors including the kind and extent of the response sought to be achieved, other ingredients of the composition to be administered, patient's age, weight, general health state, sex and diet, route of administration, excrement rate, treatment duration, drugs mixed with or concurrently administered together with the composition, and other factors well known in the medical art.

Mammals including humans fall within the range of the subject to which the composition is administered. Among them are cow, pigs, horses, rabbits, humans and mice.

As used herein, the term "administration" is intended to refer to the introduction of the pharmaceutical composition according to some embodiments of the present invention into a patient by a suitable route. As long as it allows the composition according to some embodiments of the present invention to reach a target tissue, any oral or parenteral route may be used.

In accordance with still a further aspect thereof, the present invention pertains to the use of the peptide of Sequence Formula I in the preparation of a composition for wound healing or regenerating skin cells.

The antimicrobial peptides according to some embodiments of the present invention exhibit inhibitory activity against antibiotic-resistant strains, and their antimicrobial activity is maintained without loss of structural stability even under a high salt condition. Also, being proven to promote the migration and regeneration of skin cells in mice as well as in vitro, the antimicrobial peptides according to some embodiments of the present invention may be widely used as an agent for regenerating skin cells. Further, they can find applications in various fields including the medical industry and the cosmetic industry. Hence, the novel antimicrobial peptides according to some embodiments of the present invention are anticipated to have considerable repercussions in the market for antibiotics, wound healing agents and cosmetics.

A better understanding of some embodiments of the present invention may be obtained through the following examples which are set forth to illustrate, but are not to be construed as limiting the present invention.

Example 1

Synthesis of Peptides

The peptides of the following sequences amidated at their C-terminal ends, which correspond to the antimicrobial peptides designed to maintain high antimicrobial activity at as high a salt concentration as the one in the body (Korean Patent No. 10-0836596) and to contain the basic amino acids arginine (R) and lysine (K), were synthesized using solid/solution phase Fmoc-chemistry, followed by purification by high-performance liquid chromatography. Finally, the peptides with a purity of 97% or higher were employed in the experiments.

```
Peptide 17:   APKAMKLLKKLLKLQKKGI    (SEQ ID NO. 1)

Peptide 26:   APKAMRLLRRLLRLQKKGI    (SEQ ID No. 2)
```

Example 2

Assay of Peptides for Ability to Promote Skn Cell Migration

To examine whether each of the peptides synthesized in Example 1 could promote the migration of skin cells, a boyden chamber assay was used.

In the chamber of two compartments separated by a microporous membrane, 50 μL of a suspension containing the human skin cell HaCat at a concentration of $5 \times 10^3$ CFU/ml was placed in the upper compartment and were allowed to migrate through the pores of the membrane into the lower compartment in which a 0.25~16 μM dilution of each of the peptides in a skin cell culture medium was present. The cells which migrated into the lower compartment were counted to determine the ability of each of the peptides to promote skin cell growth (FIG. 1). For a control, a skin cell culture medium containing none of the peptides was used.

The rates of the skin cell migration induced by Peptides 17 and 26 are plotted in FIGS. 1A and 1B, respectively. As seen in FIGS. 1A and 1B, the most effective migratory activity was obtained in the presence of 1 μM of each of the peptides, corresponding to about 4.5 times that of the control. Therefore, the peptides according to some embodiments of the present invention were found to promote the migration of skin cells.

Example 3

Assay of the Antimicrobial Peptides for Activity of Regenerating Skin Cells

To examine whether each of the peptides synthesized in Example 1 can enhance the regeneration of skin cells, a scratched wound-healing assay was used.

900 μL of a suspension containing HaCat at a concentration of $1 \times 10^5$ CFU/ml was placed in each well of 12-well plates and incubated for 3 days. 1 μM of each of the peptides, which was proven to induce the most effective migration rate of skin cells, was added to each well. A clear zone was set at the center of each well of the plate using a yellow tip. After incubation for 12 hrs, a reduced area of the clear zone was measured to determine the effect of each peptide on the regeneration of skin cells (FIG. 2). For a control, no peptides were used.

The effects of the peptides according to some embodiments of the present invention are given in a graph and photographs in FIG. 2. As seen in FIG. 2, skin cells were regenerated 2.5-fold faster in the presence of each of the peptides than in the absence of them. Therefore, the peptides according to some embodiments of the present invention are found to enhance the regeneration of skin cells.

Example 4

Therapeutic Effect of the Antimicrobial Peptides on Wounds in Mice

The effect of the peptides according to some embodiments of the invention on the regeneration of skin cells, which was proven by the in-vitro assay of Example 3, was examined in vivo.

Mice were shaved on the back using an electric razor, followed by forming a full-thickness wound 1.1 cm in diameter using surgical scissors. Application of 50 μL of 1 μM peptide 17 to the wound was continued for 2 days, after which the size of the wound was measured. The wound healing activity of peptide 17 was expressed by the reduced area of the wound (FIG. 3). As the control, the mice were treated with distilled water instead of peptide 17.

As seen in FIG. 3, the area of the wound was decreased 7-fold faster in the mice treated once a day for two days than in the mice treated with none of them. Thus, the peptides according to some embodiments of the present invention can significantly reduce the area of a wound in vivo within a short period of time to guarantee a wound healing effect (FIG. 3).

Taken together, the data obtained above demonstrated that the antimicrobial peptides according to some embodiments of the present invention retained high antimicrobial activity even at as high a salt concentration as under the physiological conditions and can promote the migration and regeneration of skin cells to heal wounds, indicating that the antimicrobial peptides can be used as promising next-generation wound-healing agents useful for cell regeneration as well as having antimicrobial activity against antibiotic-resistant strains.

What is claimed is:

1. A method of regenerating skin cells, the method comprising:

applying to an injured skin a composition promoting skin cell migration and thereby regenerating skin cells in the injured skin, the composition comprising a peptide having an amino acid sequence of SEQ ID NO. 1.

2. The method according to claim 1, wherein the peptide is amidated at the C-terminal end thereof.

3. The method according to claim 1, wherein the peptide is subjected to an in vivo salt concentration from 100 to 200 mM.

4. The method according to claim 1, wherein the composition further comprises a pharmaceutically acceptable carrier, excipient or diluents.

5. The method according to claim 1, wherein the peptide is present at a concentration of from 0.5 to 2 µM.

* * * * *

SEQUENCE LISTING

```
<160> NUMBER OF SEQ ID NOS: 3

<210> SEQ ID NO 1
<211> LENGTH: 19
<212> TYPE: PRT
<213> ORGANISM: Artificial Sequence
<220> FEATURE:
<223> OTHER INFORMATION: antimicrobial peptide 17

<400> SEQUENCE: 1

Ala Pro Lys Ala Met Lys Leu Leu Lys Lys Leu Leu Lys Leu Gln Lys
 1               5                  10                  15

Lys Gly Ile

<210> SEQ ID NO 2
<211> LENGTH: 19
<212> TYPE: PRT
<213> ORGANISM: Artificial Sequence
<220> FEATURE:
<223> OTHER INFORMATION: antimicrobial peptide 26

<400> SEQUENCE: 2

Ala Pro Lys Ala Met Arg Leu Leu Arg Arg Leu Leu Arg Leu Gln Lys
 1               5                  10                  15

Lys Gly Ile

<210> SEQ ID NO 3
<211> LENGTH: 19
<212> TYPE: PRT
<213> ORGANISM: Artificial Sequence
<220> FEATURE:
<223> OTHER INFORMATION: antimicrobial peptide 26
<220> FEATURE:
<221> NAME/KEY: MISC_FEATURE
<222> LOCATION: (6)..(6)
<223> OTHER INFORMATION: Xaa is a basic amino acid residue
<220> FEATURE:
<221> NAME/KEY: MISC_FEATURE
<222> LOCATION: (7)..(8)
<223> OTHER INFORMATION: Xaa is a hydorphobic amino acid residue,
      wherein Xaa at position 7 and Xaa at position 8 may be the same or
      different
<220> FEATURE:
<221> NAME/KEY: MISC_FEATURE
<222> LOCATION: (9)..(10)
<223> OTHER INFORMATION: Xaa is a basic amino acid residue, wherein Xaa
      at position 9 and Xaa at position 10 may be the same or different
<220> FEATURE:
<221> NAME/KEY: MISC_FEATURE
<222> LOCATION: (11)..(12)
<223> OTHER INFORMATION: Xaa is a hydorphobic amino acid residue,
      wherein Xaa at position 11 and Xaa at position 12 may be the same
      or different
<220> FEATURE:
<221> NAME/KEY: MISC_FEATURE
<222> LOCATION: (13)..(13)
<223> OTHER INFORMATION: Xaa is a basic amino acid residue

<400> SEQUENCE: 3
```

```
Ala Pro Lys Ala Met Xaa Xaa Xaa Xaa Xaa Xaa Xaa Xaa Leu Gln Lys
 1               5                  10                  15
Lys Gly Ile
```